United States Patent [19]
Lee et al.

[11] Patent Number: 5,889,146
[45] Date of Patent: Mar. 30, 1999

[54] METHOD FOR SYNTHESIS OF BIFUNCTIONAL CHELATING AGENTS-PEPTIDES

[75] Inventors: Te-Wei Lee; Shui-Tein Chen, both of Taipei; Shiang-Rong Chang; Shyh-Yi Chyi, both of Tau Yen; Chang-Mau Shing, Taipei; Tian-Fu Huang, Tau Yen; Lie-Hang Shen, Tau Yen; Zei-Tsan Tsai, Tau Yen; Kung-Tsung Wang; Gann Ting, both of Taipei, all of Taiwan

[73] Assignee: Institute Of Nuclear Energy Research, Tau-Yen, Taiwan

[21] Appl. No.: 978,615

[22] Filed: Nov. 26, 1997

[51] Int. Cl.$^6$ .............................. A61K 38/12; C07K 5/00; C07K 7/00; C07K 17/00

[52] U.S. Cl. .............................. 530/317; 530/333; 514/9; 514/11

[58] Field of Search .................................... 530/317, 384; 514/9, 11

[56] References Cited
PUBLICATIONS

Krenning et al, *J. of Nuclear Medicine,* vol. 33 No. 5, pp. 652–658, May, 1992.
Bakker et al, Life Sciences, vol. 49, pp. 1593–1601, 1991.

*Primary Examiner*—Cecilia J. Tsang
*Assistant Examiner*—S. G. Marshall
*Attorney, Agent, or Firm*—Rosenberg, Klein, & Bilker

[57] ABSTRACT

This invention is a novel synthesis of BCA-peptides (BCA: bifunctional chelating agents). In this method, the starting material—Fmoc-Thr(ol)-Terephthal-Acetal-Amide Resin is coupled with the various amino acids. The straight peptide-resin of D-Phe-Cys(Trt)-Phe-D-Trp(Boc)-Lys(Boc)-Thr(tBu)-Cys(Trt)-Thr(ol)-Terephthal-Acetal-Amide Resin was obtained. This compound reacted with iodine to give disulfide-containing peptide resin of

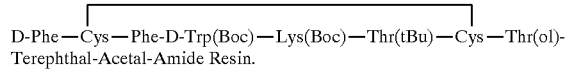

D-Phe—Cys—Phe-D-Trp(Boc)—Lys(Boc)—Thr(tBu)—Cys—Thr(ol)-Terephthal-Acetal-Amide Resin.

Cleavage of the peptide from the resin was achieved by TFA. The cleavaged peptide was protected by the reaction of octreotide with di-t-butyldicarbonate. BCA was coupled to the selectively protected octreotide. This product was obtained by reaction of protected BCA-peptides with TFA. The final product was labeled by radioisotope $^{111}$InCl$_3$ for tumor imaging radiopharmaceuticals.

6 Claims, No Drawings

METHOD FOR SYNTHESIS OF BIFUNCTIONAL CHELATING AGENTS-PEPTIDES

FIELD OF THE INVENTION

The present invention relates to a novel synthesis of octreotide by solid phase synthesis and conjugated peptides using bifunctional chelating agents. In particular, the present invention relates to linkage, cyclization, and radioactive isotope labelling such as by In-111 or Y-90.

BACKGROUND OF THE INVENTION

Radiolabeled somatostatin analog, $^{111}$In-DTPA-octreotide, this new scintigraphic technique has attracted great interest in clinical nuclear medicine. The radiopharmaceutical has been used successfully for the localization of primary and metastatic somatostatin receptor-rich tumors, such as carcinoid, islet cell tumors of the pancreas, paragangliomas and small-cell carcinomas of the lungs. Octreotide comprises 8 amino acids which has the following structural formula:

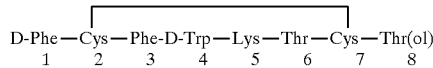

wherein the sulfur atoms of the Cys at the position 2 and of the Cys at the position 7 are mono-cyclic to form an —S—S— bridge. When conjugated to the chelate diethylenetriaminepentaacetic acid (DTPA) and labeled with $^{111}$In, The product of $^{111}$In-DTPA-octreotide is a useful single-photon emission computed tomographic(SPECT) imaging agent for tumors containing somatostatin receptors. Synthesis of DTPA-octreotide can be carried out by two methods. The first method is synthesized initially by fragment condensation solution-phase procedures for octreotide. The synthetic process of octreotide has been described by Baner et al. in U.S. Pat. No. 4,395,403 in 1983. The process comprises:

<i>removing protected group from peptide;
<ii>linking together by an amide bond two peptide unit;
<iii>converting a function group at the N- or C-terminal;
<iv>oxidizing a straight chain polypeptide by borontristrifluoroacetate.

This process involves a time-consuming, multi-step synthesis, and it is difficult to separate octreotide from the reaction mixtures since all the synthesis steps are carried out in liquid phase.

DTPA-octreotide was synthesized by protecting the N$^ε$-amine group of the lysine residue of octreotide with a Boc group, followed by condensation of the unprotected N$^α$-amine group with DTPA.

The second method is synthesized by solid-phase procedure for DTPA-octreotide (J. Med. Chem. 1994, 37, 3749–3757). The procedure reacted DTPA with protected octreotide precursor on resin, before aminolysis with threoninol, followed by deprotection of Boc groups of D-Trp$^4$, Lys$^5$, and tBu group of Thr with trifluoroacetic acid (TFA). The overall synthetic yield of DTPA-octreotide by this protocol was 5%. The present invention provides a solid-phase synthesis of octreotide using 9-fluorenylmethoxycarbonyl(Fmoc) methodology. Octreotide was conjugated with bifunctional chelating agent in solution-phase.

SUMMARY OF THE INVENTION

The main object of the present invention is to provide a new method for synthesis of BCA-octreotide where BCA is a bifunctional chelating agent.

Octreotide has been synthesized using Fmoc method of solid-phase synthesis. In this method, the starting material Fmoc-Thr(ol)-Terephthal-Acetal-Amide Resin, is coupled with the various amino acids. The straight chain of peptide-resin compound Fmoc-D-Phe-Cys(Trt)-Phe-D-Trp(Boc)-Lys(Boc)-Thr(tBu)-Cys(Trt)-Thr(ol)-Terephthal-Acetal-Amide Resin was suspended in DMF and treated with iodine.

Disulfide-containing peptide-resin of

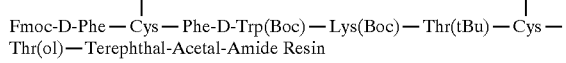

can be obtained when oxidation is carried out on peptide chain anchored to polymeric supports. Cleavage of the peptide from the resin was achieved by trifluoroacetic acid (TFA). Purification of the crude peptide of

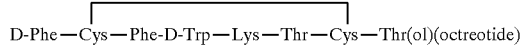

has been accomplished in a one-step procedure using reverse-phase high performance liquid chromato-graphy (HPLC).

The reaction of octreotide with di-t-butyldicarbonate [(Boc)$_2$O] forms protected octreotide. BCA was coupled to the selectively protected octreotide. The product was obtained by reaction of protected BCA-octreotide with TFA.

The novel method in this invention for synthesis of BCA-octreotide has been proved to be more time-saving and easier for separation from the reaction system than the prior art is. The final product was labeled by radio-isotope for radiopharmaceuticals.

DETAILED DESCRIPTION OF THE INVENTION

The following abbreviations are employed:
Fmoc: 9-fluorenylmethoxycarbonyl
Boc: t-butyloxycarbonyl
tBu: tert-butyl
Trt: triphenylmethyl
Thr(ol): threoninol residue
Phe: phenylalanine residue
Cys: cysteine residue
Thr: threonine residue
Lys: lysine residue
Trp: tryptophan residue
TFA: trifluoroacetic acid
EDT: 1,2-ethanedithiol
DTPA: diethylenetriaminepentaacetic acid
DOTA: 1,4,7,10-tetraazacyclododecane-N,N',N'',N'''-tetraacetic acid
DMSO: dimethylsulfoxide
(Boc)$_2$O: di-tert-butyldicarbonate
DIEA; N-ethyl-diisopropylamine
PBS: phosphate buffer saline
DMF: N,N-dimethylformamide
BCA: bifunctional chelating agent
THF: tetrahydrofuran
HBTU: [2-(1H-benzotriazol-1-yl)-1,1,3,3-tetramethyluronium hexafluorophosphate]
DIEA: N,N-diisoprepylethylamine The practice of the invention is further illustrated by the following examples, but the illustration doesn't limit the scope of this application.

EXAMPLE 1

Synthesis of Fmoc-Thr-CH₂OH

N-(9-Fluorenylmethoxycarbonyl)-Threonine(N-Fmoc-Thr)(1.7 g, 5 mmol) was dissolved in 50 mL of anhydrous THF, and 50 mL of 1M BH₃.THF added dropwise through addition funnel over a period of 10 min. The resulting mixture was then stirred at room temperature for 8 hrs. The reaction mixture was quenched with 50 ml of 1N HCl1. After stirring at room temperature for 1 hr, the mixture was diluted with 40 mL of water and 100 ml of a THF/diethyl ether (1:1) mixture. The organic layer was separated and the aqueous layer extracted with two 60 mL portion of the THF/ether(1:1) mixture. The combined organic layers were then washed with brine (2×125 mL), 1.5N KOH (2×125 mL), and brine (2×125 mL), dried with Na₂SO₄, filtered, concentrated in vacuo, and purified by flash chromatography (ethyl acetate:n-hexane=4:1) to afford 1.3 g white solid (80%) of Fmoc-Thr-CH₂OH(Rf=0.34 in ethyl acetate:n-hexane=4:1).

Melting Point(mp). 100°~102° C.;

FAB-MASS(m/z):328(M+1),179, 178.

$^1$H—NMR(CDCl₃):δ7.73(2H,d,7.5 Hz),7.57(2H,d,7.4 Hz),7.37(2H,t,7.4 Hz),7.28(2H,t,7.4 Hz),5.58(1 H,d,8.8 Hz),4.43–4.37(2H,m),4.19–4.09(2H,m),3.37(2H,d,4.2 Hz), 3.58–3.50(1H,br),1.16(3H,d,6.3 Hz);

$^{13}$C—NMR(CDCl₃): δ157.06, 143.75, 141.28, 141.24, 127.68, 127.03, 124.98, 119.95, 68.38, 66.71, 64.57, 56.05, 47.18, 20.22.

EXAMPLE 2

Synthesis of Fmoc-Thr-CH₂OH-Terephthal-Acetal

A mixture of Fmoc-Thr-CH₂OH(0.3 g, 0.9 mmol), p-carboxybenzaldehyde(0.34 g, 2.25 mmol), a few crystals of p-toluenesulfonic acid, and two drops of dimethylsulfoxide in CHCl₃(30 ml) was heated overnight under nitrogen with a Crankcase dilution trap to remove water. After the mixture was cooled, the solvent was evapored under reduced pressure to provide a yellow oil.

Flash chromatography of the residue over silica gel using methylene chloride:ethyl acetate (3:1) as eluent furnished the desired product (275 mg, 65%)(Rf=0.28 in methylene chloride:ethyl acetate=3:1).

mp.86°–88° C.;

FAB-MASS(m/z): 460(M+1), 179, 178, 154, 136.

$^1$H—NMR(CDCl₃): δ10.11(1H,S),8.13(2H,d,8.3 Hz), 7.75(2H,d,7.5 Hz),7.60–7.55(4H,m),7.41–7.28(4H,m), 5.63–5.56(2H,m),4.47–4.42(2H,m),4.25–4.12(4H,m),3.71 (1H,d,4.2 Hz),1.27(3H,m);

$^{13}$C—NMR (CDCl): δ171.13, 156.54, 143.81, 143.05, 141.30, 130.21, 129.87, 127.70. 127.04, 126.13, 125.02, 119.98, 100.73, 75.44, 71.81, 66.96, 48.70, 47.24, 17.52.

EXAMPLE 3

Synthesis of D-Phe-Cys(Trt)-Phe-D-Trp(Boc)-Lys(Boc)-Thr(tBu)-Cys(Trt)-Thr(ol)-Terephthal-Acetal-Amide Resin Fmoc-Thr(ol)-Terephthal-Acetal-Amide Resin (1 mmole) was used as the starting material for solid-phase peptide synthesis. The Fmoc protecting group of Fmoc-Thr(ol)-Terephthal-Acetal-Amide Resin was removed by piperidine. Fmoc-Cys(Trt)-OH was activated by using HBTU.

In the coupling step, the activated Fmoc-Cys(Trt)-OH reacted with Thr(ol)-Terephthal-Acetal-Amide Resin to form Fmoc-Cys(Trt)-Thr(ol)-Terephthal-Acetal-Amide Resin. Deprotecting and coupling steps are repeated with each subsequent amino acid until an assembly chain D-Phe-Cys(Trt)-Phe-D-Trp(Boc)-Lys(Boc)-Thr(tBu)-Cys(Trt)-Thr(ol)-Terephthal-Acetal-Aamide Resin has been completed.

The peptide resin was further treated with 2.5% EDT-2.5% H₂O-95% TFA for 3 hr to form a compound giving a major peak on analytical reversed-phase high performance liquid chromatography. Positive ion electrospray mass spectra (ESMS) analysis of the isolated peak suggests the compound has a structure D-Phe-Cys-Phe-D-Trp-Lys-Thr-Cys-Thr(ol), as [M+H]⁺=1021 Da.

EXAMPLE 4

Synthesis of

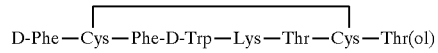
D-Phe—Cys—Phe-D-Trp—Lys—Thr—Cys—Thr(ol)

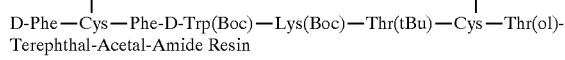
D-Phe—Cys—Phe-D-Trp(Boc)—Lys(Boc)—Thr(tBu)—Cys—Thr(ol)-Terephthal-Acetal-Amide Resin (200 mg, 0.0491 mmol) was suspended in DMF. This solution of peptide-resin was added by dropwise to a vigorously stirred solution of iodine(249 mg) in DMF. After a reaction time of 1 hr, excess iodine was washed with DMF. The product of

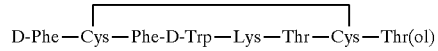
D-Phe—Cys—Phe-D-Trp—Lys—Thr—Cys—Thr(ol)

was reductively cleavaged as described in Example 3. The analytic result gave [M+H]⁺=1019 Da by ESMS

EXAMPLE 5

Synthesis of

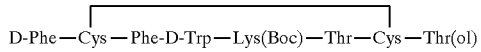
D-Phe—Cys—Phe-D-Trp—Lys(Boc)—Thr—Cys—Thr(ol)

The crude octreotide

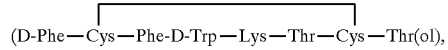
(D-Phe—Cys—Phe-D-Trp—Lys—Thr—Cys—Thr(ol), 101.9 mg, 0.1 mmol) was dissolved in 5 mL of DMF. To this solution was added 21 μl of (Boc)₂ O, and the mixture was stirred at room temperature for 3–4hrs. After the mixture was concentrated in vacuo, the crude product was purified by HPLC. Fractions containing the peptide were collected, and the solvent was removed by lyophilization to afford 80 mg of D-Phe-Cys-Phe-D-Trp-Lys(Boc)-Thr-Cys-Thr(01) as a white powder.

The analytic result gave [M+H]⁺=1120 Da by ESMS.

EXAMPLE 6

Synthesis of [DTPA-D-Phe¹]-octreotide

DTPA anhydride (3.3 mg) dissolved in 15 ml of DMF and 29 μl of DIEA mixture.

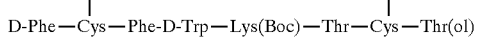

(9.4 mg) in 7 ml of DMF was added to the mixture. After stirring at room temperature for 1 hr, the solvent was evapored under reduced pressure. The residues were treated with 3 ml of 95% TFA for 5 min and concentrated in vacuo.

The crude product was dissolved in 50% acetonitrile and purified by HPLC (10×250 mm $C_{18}$ column) using a gradient of 90–10% A in 40 min at a flow rate of 2 ml/min, where A=0.1% TFA in $H_2O$ and B=0.1% TFA in acetonitrile. The product peak eluting at 24.2 min gave $[M+H]^+=1395$ Da by ESMS.

EXAMPLE 7

Synthesis of [DOTA-D-Phe']-octreotide

DOTA (30 mg) was dissolved in 10 ml of DMF and triethylamine mixture(4:1 v/v). Isobutyl chloroformate (26.5 μl) was added dropwise at 0° C. to the mixture. After 20 min, the protected (t-butyloxycarbonyl-Lys$^5$)-octreotide was added and the reaction was kept at roon temperature for 5 hr. The mixture was concentrated in vacuo and the residues were treated with 3 mL of 95% TFA for 5 min and concentrated in vacuo. The crude product was purified by HPLC using a 10×250 mm $C_8$ column with a flow rate of 2 ml/min. A 40 min linear gradient, from 70–10% A (A:0.1%TFA in $H_2O$; B:0.1%TFA in acetonitrile) was used. The major peak at retention time 14 min was collected. ESMS analysis of the isolated peak showed $[M+H]^+=1406$ Da.

EXAMPLE 8

In-111 labeling of [DOTA-D-Phe$^1$]-octreotide

[DOTA-D-Phe$^1$]-octreotide (5 μg) was dissolved in 20 μl of 0.1M sodium acetate (pH 5). $^{111}InCl_3$(2 mci in 0.1M sodium acetate, PH 5) was added to the [DOTA-D-Phe$^1$]-octreotide solution and incubated at room temperature for 1 hr.

The solution was then loaded onto a $C_{18}$ SepPak cartridge, washed with sodium acetate buffer, and eluted with 1 ml of PBS. Quality analysis was done on ITLC (SG) with sodium citrate pH 5 to determine $^{111}$In-[DOTA-D-Phe$^1$]-octreotide (Rf=0) and $^{111}InCl_3$ (Rf=1). The labeling efficiency was more than 95%.

EXAMPLE 9

$^{111}$In Labeling of [DTPA-D-Phe$^1$ ]-octreotide

The labeling of [DTPA-D-Phe$^1$]-octreotide with $^{111}InCl_3$was by procedures analogous to those described in Example 8 (>96% labeling efficiency).

We claim:

1. A method for synthesis of BCA-peptides comprising the following steps:

(1) using Fmoc-Thr(01)-Terephthal-Acetal-Amide Resin as the starting material, coupling of various selected amino acid residues to give the straight chain peptide compound;

(2) oxidizing the straight chain peptide-resin, then cleaving the oxidized peptide of a mono-cyclic chain from the resin to the liquid phase, and deprotecting the cleavaged peptide to obtain the product as formula (I); and

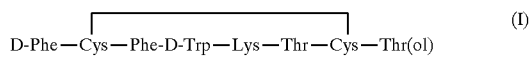

(I)

(3) then the formula (I) compound is added to di-t-butyldicarbonate, then BCA coupling with protected peptide, and deprotecting the cleavaged peptide to obtain the product as formula (II)

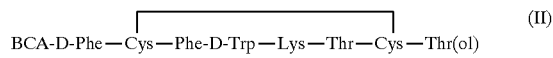

(II)

2. The method for synthesis of BCA-peptides according to claim 1, wherein in step (1), said straight chain peptide-resin compound has the formula Fmoc-D-Phe-Cys(Trt)-Phe-D-Trp(Boc)-Lys(Boc)-Thr(tBu)-Cys(Trt)-Thr(01)-Terephthal-Acetyl-Amide Resin.

3. The method for synthesis of BCA-peptides according to claim 1, wherein in step (2), said oxidizing the straight chain peptide-resin which comprises the steps of reacting peptide-resin compound with iodine to form a mono-cyclic chain of peptide of formula

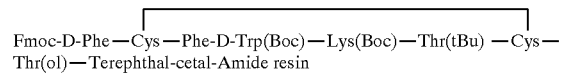

4. The method for synthesis of BCA-peptides according to claim 1, wherein in step (3), said formula (I) compound added to di-t-butyldicarbonate has the formula

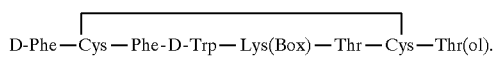

5. The method for synthesis of BCA-peptides according to claim 1, wherein in step (3), said BCA is DTPA or DOTA.

6. The method for synthesis of BCA-peptides according to claim 1, further including the step of labeling said formula (II) with In-111.

* * * * *